(12) United States Patent
Bufe et al.

(10) Patent No.: US 6,731,311 B2
(45) Date of Patent: May 4, 2004

(54) PATIENT MONITOR WITH CONTINUOUS STATUS DISPLAY

(75) Inventors: Martin Bufe, Ebersbach (DE); Wilhelm Meier, Herrenberg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 20 days.

(21) Appl. No.: 09/778,189

(22) Filed: Feb. 7, 2001

(65) Prior Publication Data

US 2001/0014769 A1 Aug. 16, 2001

(30) Foreign Application Priority Data

Feb. 11, 2000 (EP) ............................................. 00102810

(51) Int. Cl.[7] ................................................. G09G 5/00
(52) U.S. Cl. ....................... 345/781; 345/791; 345/794; 600/301
(58) Field of Search ........................... 600/301; 345/133, 345/700, 733, 764, 779, 781, 790, 791, 794

(56) References Cited

U.S. PATENT DOCUMENTS

| 5,325,478 A |   | 6/1994 | Shelton et al. |
|---|---|---|---|
| 5,331,549 A |   | 7/1994 | Crawford |
| 5,482,050 A | * | 1/1996 | Smokoff et al. ............ 345/788 |
| 5,631,825 A |   | 5/1997 | Weele et al. |
| 5,752,917 A | * | 5/1998 | Fuchs .......................... 600/484 |
| 5,921,920 A | * | 7/1999 | Marshall et al. ............ 600/300 |
| 6,287,252 B1 | * | 9/2001 | Lugo ........................... 600/300 |

OTHER PUBLICATIONS

European Search Report (EP00 10 2810), Completed on Jul. 20, 2000 by Examiner D. Lemercier of the European Patent Office.

* cited by examiner

*Primary Examiner*—Cao (Kevin) Nguyen
*Assistant Examiner*—Brian Detwiler

(57) ABSTRACT

A patient monitoring system includes a plurality of patient monitors, each for monitoring the physiological condition of a local patient connected with respective patient monitor, whereby the patient monitors provide a data-communication with each other. Each patient monitor comprises a display adapted for displaying information representative of the physiological condition of the local patient. The display of at least one of the patient monitors comprises an overview area for displaying status information from one or more of the other patient monitors.

18 Claims, 5 Drawing Sheets

PATIENT MONITOR WITH CONTINUOUS STATUS DISPLAY

BACKGROUND OF THE INVENTION

The present invention relates to patient monitors for monitoring the physiological condition of a patient, in particular networked patient monitors.

One of the most important tasks of bedside patient monitoring is the generation of alarms. If, as shown in a typical example in FIG. 1, a plurality of bedside monitors BEDi (with i=1 to 16 in FIG. 1) are connected via a network 20, an alarm status of each bedside monitor BEDi can be distributed to a central station 30 or to any other of the bedside monitors BEDi. The central station 30 is normally located remote from the bedside monitors BEDi.

The central station 30 typically allows displaying status and real time data of all or a subset of the connected bedside monitors BEDi. The central station 30 further generally allows to view one individual bedside monitor BEDi in greater detail provided in a specific window, as e.g. by the Patient Window of the Agilent Information Center of Agilent Technologies. The Remote Link product of Agilent Technologies allows remotely viewing information from different bedsides similar to a central station e.g. in a doctor's office. It does not trigger any alarms, but displays patient status in a comprehensive overview (color coded boxes), and similar to a central station allows to overview more data of a single bed in a window.

As depicted in FIG. 2, existing networked bedside monitors BEDi usually provide a display 100 showing data, such as alarms and/or measured data, from the local bedside monitor BEDi. Data of another (remote) bedside monitor BEDj (with j≠i) can be selected by means of buttons 110 (e.g. soft or hard keys) and displayed in a pop-up window 120 generally overlapping the data display of the local bedside monitor BEDi. Alternatively, the pop-up window 120 and an alarm tone can appear when another bedside monitor BEDj goes into an alarming state. A manual navigation scheme generally allows viewing other bedside monitors BEDi independent of an alarming situation.

SUMMARY OF THE INVENTION

Although the existing bedside monitors already provide precious tools for monitoring a patient's physiological condition, it is still required to further improve patient monitoring, in particular in networked applications.

The object is solved by the independent claims. Preferred embodiments are shown by the dependent claims.

The invention provides a way of helping clinical staff to assess the status of a plurality of patients at one glance by permanently presenting the status of a plurality of bedside monitors on a reserved area of each bedside monitor. This status information is provided continuously and independently of an alarming situation. Preferably, the reserved area for this status information is displayed in a side area of the monitor display and/or separated from other data to be displayed (such as data from a local or remote bedside monitor). Thus, the invention allows providing a comprehensive overview over the related bedside monitors without disturbing local operations or data monitoring, e.g. by pop-up windows covering or overlapping the data display.

The term "related monitors" as used herein shall represent a plurality of monitors connected with each other, e.g. by means of a data network, thus allowing a data communication between the monitors. Accordingly, the term "monitor" as used herein shall represent any kind of patient monitor applicable for monitoring physiological information of a patient.

By displaying a continuous status information for related bedside monitors, the invention overcomes a disadvantage of conventional bedside monitors, which normally only render available information about other bedside monitors in case of an alarm or after a user interaction, however always only the information of one bedside monitor is displayed at the same time. Furthermore, the invention preferably allows providing such status information generally without overlapping other data display.

For fully appreciating the contribution of the invention, it has to be understood that although a patient monitor might resemble a conventional computer to a certain degree, the patient monitor still represents a measuring device. The main purpose of a measuring device, however, is to measure data and make the measured data available e.g. by displaying the measured data. Therefore, it is important for measuring devices that essential information will be made available and is not accidentally suppressed e.g. by being overlapped. This is in particular of relevance for patient monitoring where a patient's physiological signals are monitored and where a not-showing of vital information can cause serious harm to the patient. A continuous display of status information also of other related bedside monitors, however without interfering with the selected display therefore represents a significant improvement for patient monitoring applications.

In a preferred embodiment of the invention, an area of a screen of a patient monitor is allocated for displaying the status information in an overview area. The overview area remains preferably allocated permanently or at least as long as defined by the respective application or by a user. The remaining area of the screen can be used for displaying other kind of information, e.g. to show data of the local patient connected to the respective patient monitor, or to view (e.g. in greater detail) information from other patient monitors, but also for increasing the overview area.

The location and the size of the overview area depend on the specific screen configurations. It is also clear that the overview area needs not necessarily be a static area fixed to a certain location, but is also moveable along the screen. However, the overview area is preferably spatially separated from the other display areas and will preferably not or only temporarily overlap or be overlapped therewith.

The overview area allows to concurrently display the status of other patient monitors connected to that patient monitor e.g. via a network. This status of other patient monitors is preferably displayed using symbols, codes or pictograms. Alternatively or in addition thereto, this status information can also be provided with alphanumerical text fields, e.g. for indicating a specific alarming state or the other patient's name.

In a preferred embodiment, the size of the overview area can be further increased in order to display more or more detailed information about one or more of the other related patient monitors, and/or decreased to reduce the information content displayed. Preferably, the overview area can only be reduced in size until a predefined minimum, which still enables to overview the other patient monitors.

In another preferred embodiment, the overview area provides entry points for operations to get more information from a related patient monitor and/or to involve a remote operation (e.g. a button to silence an alarm or to show a window to change alarm limits).

It is clear that the invention can be partly or entirely embodied by one or more suitable software programs, which can be stored on or otherwise provided by any kind of data carrier, and which might be executed in or by any suitable data processing unit.

BRIEF DESCRIPTION OF THE DRAWINGS

Other objects and many of the attendant advantages of the present invention will be readily appreciated and become better understood by reference to the following detailed description when considering in connection with the accompanied drawings. Features that are substantially or functionally equal or similar will be referred to with the same reference sign(s).

DETAILED DESCRIPTION OF THE INVENTION

Figure 2:
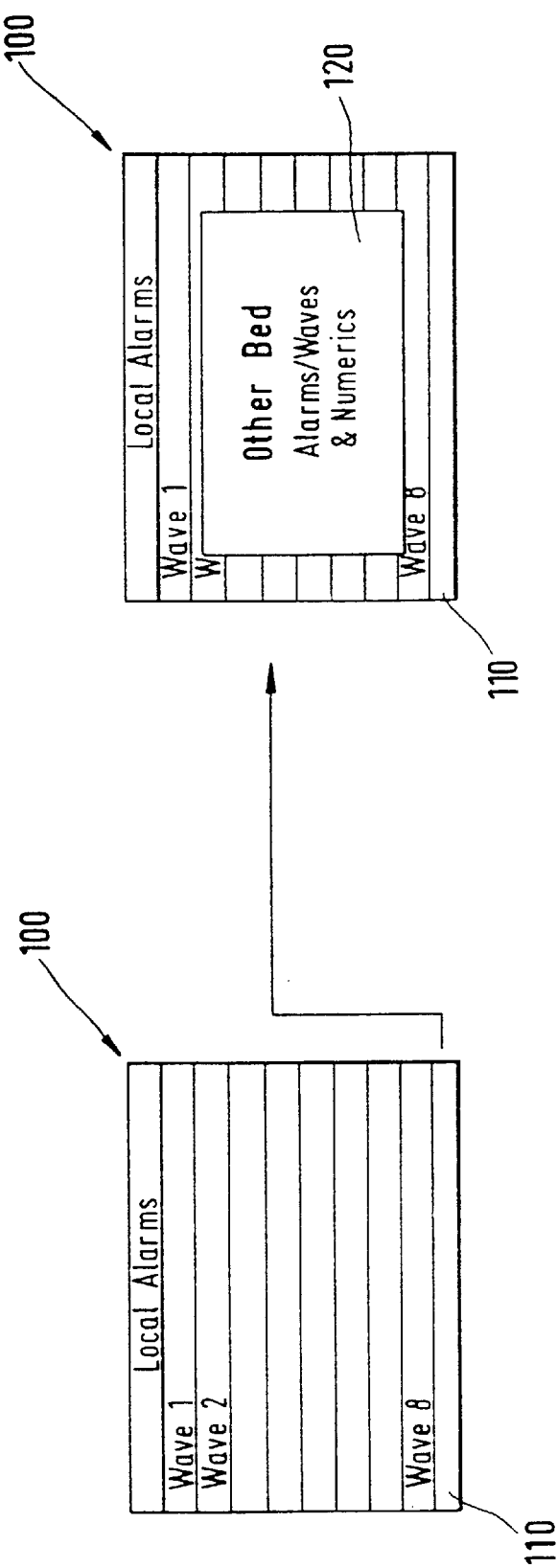
FIG. 2 depicts a display of an existing networked bedside monitor.
Figure 3:
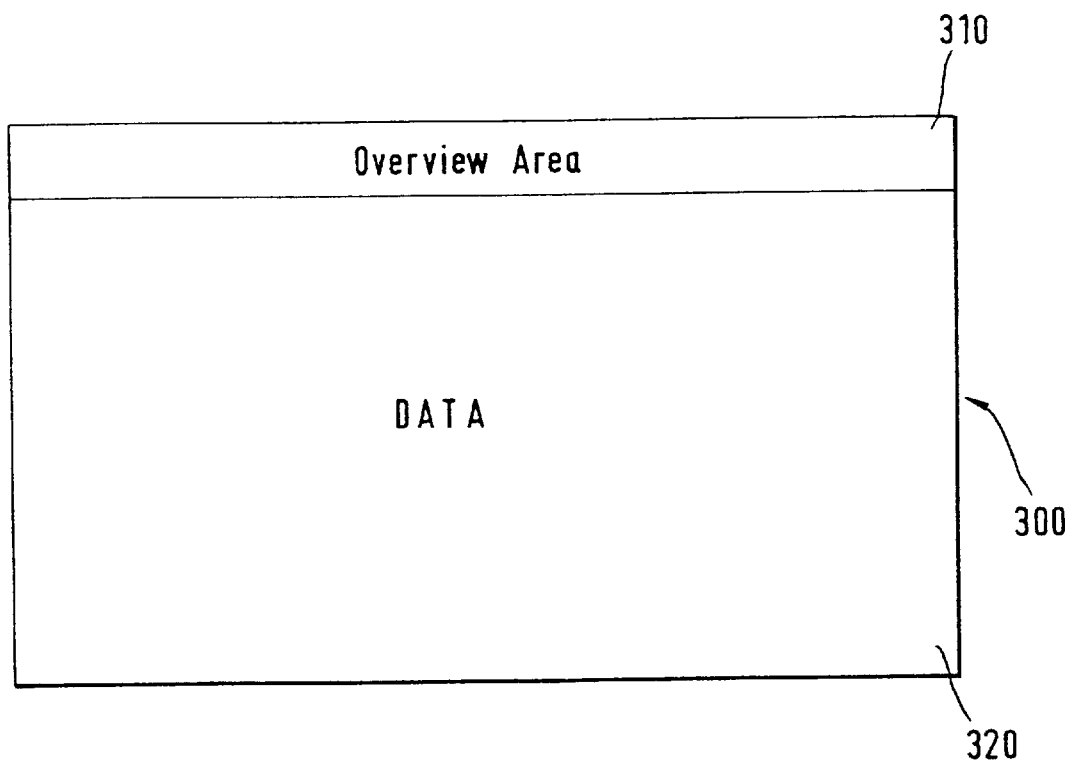
FIG. 3 shows a screen 300 of a (local) patient monitor according to a preferred embodiment of the invention.

FIG. 3 shows a screen 300 of a (local) patient monitor according to a preferred embodiment of the invention. An area of the screen 300 is allocated as an overview area 310 for continuously displaying status information of other (remote) patient monitors connected with the local patient monitor e.g. via a data network. The remaining space of the screen 300 or parts thereof can be used as a data display 320, e.g. to show data (such as alarms, numeric signs, graphical data curves (waves), or status information) of a local or a remote patient. The data display 320 can represent the display 100 of FIG. 2.

The location and the size of the overview area 310 depend on the specific configuration of the screen 300 and can be defined by a software designer or a sophisticated user.

In a normal mode of a preferred embodiment, the overview area 310 is completely separated from the data display 320, so that neither the data display 320 itself nor any dialog window will overlay and cover the overview area 310. The normal mode can be left temporarily, e.g. on user request, and the overview area 310 and the data display 320 might be overlapped shortly.

Figure 1:
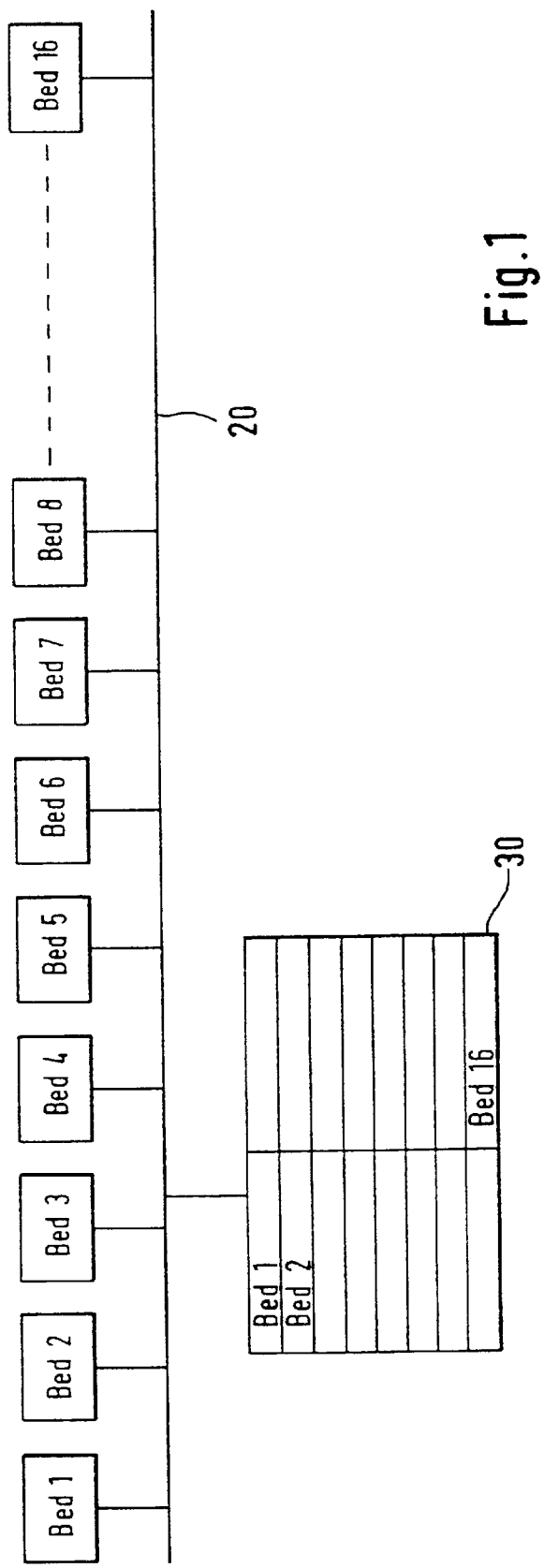
FIG. 1 shows a typical example of bedside monitors connected via a network 20, as known in the art.

The overview area 310 is used to display the status of other related patient monitors connected with the local patient monitor (e.g. as shown in FIG. 1).

Preferably, the number of other patient monitors of which the status can be displayed in the overview area 310 can be limited to a specific set of patient monitors. Such limitations can preferably be provided according to personal criteria, e.g. the patient monitors of a care group (which is usually taken care by one nurse or a specific group of nurses), or according to locality criteria, e.g. the patient monitors of a specific room in a hospital. This status information is preferably displayed by means of symbols, pictograms, codings and/or alphanumeric signs.

Figure 4A:
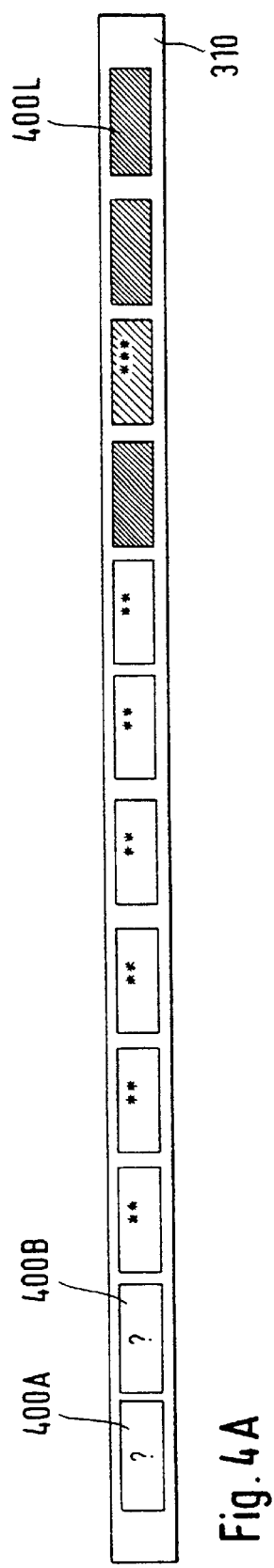
FIGS. 4A–D illustrate examples of overview areas 310 according to the present invention.

FIG. 4A shows an example for the overview area 310. In that example, the status of up to 12 related patient monitors could be displayed in the overview area 310. For each related patient monitor, a specific status field 400A, 400B, . . . , 400L is reserved. The spatial arrangement of the status fields 400 preferably corresponds with the actual physical arrangement of the respective patient monitors and/or beds, e.g. in a way that the order of the status fields 400 represents the physical or spatial order of the corresponding beds in that (care) group. The assignment of the status fields 400 to the respective beds will preferably be maintained and will only change when required. For better recognition, the status fields can be grouped, e.g. in groups of four.

In FIG. 4A, a specific coding scheme is applied, e.g.:
Bed not online or off: dark blue background
Bed online and no alarm: white box with dark blue background
Technical alarm: "-?-" with light blue (cyan) background
Limit alarm: "**" (blinking) with yellow background
Severe alarm: "***" (blinking) with red background
Alarms turned off red crossed out bell on white background
Demo mode: "DEMO" with dark blue background
Stand-by mode: "standby symbol" with dark blue background
Local bed: white box with black background.

It is clear that a different coding and/or (graphical) presentation stile can be used accordingly.

Figure 4B:
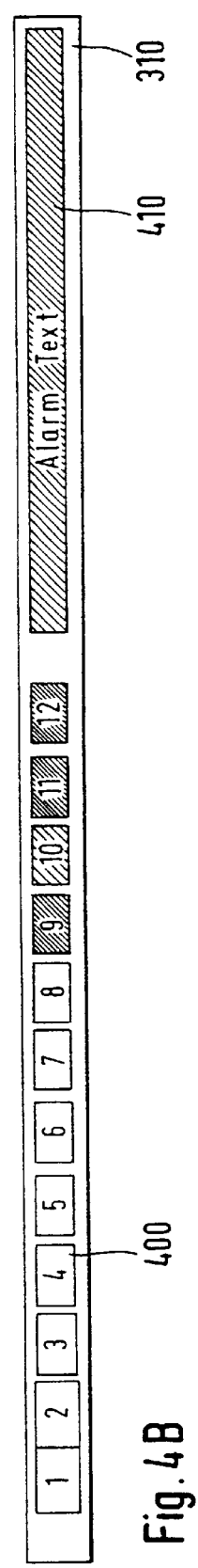

FIG. 4B shows another example of the overview area 310 with status fields 400 and one or more alarm text fields 410 (only one text field is shown in FIG. 4B). In addition to the status fields 400, active alarm texts and/or the respective patient name from other related patient monitors could be displayed in the text field(s) 410. If more alarms from different beds are active at the same time, the related alarm texts are preferably rotated in the alarm text field(s), and the related status field 400 is highlighted respectively.

While the overview area 310 in the examples of FIGS. 4A and 4B only displays status fields 400 of other related (remote) patient monitors, it is clear that one status field 400 can also be reserved for the local patient monitor. This is in particular useful when the data display 320 will be applied for displaying data of a remote patient monitor. In such a case, however, the status fields 400 might also be adapted automatically to the present display at the data display 320, so that when the data display 320 displays information of a remote patient monitor (instead of the local patient monitor) the status field of that remote patient monitor will be automatically exchanged against a status field for the local patient monitor. A reservation of one status field for the local patient monitor irrespectively of the current display in the data display 320 might also be useful for improve an intuitive understandability of the overview area 310, e.g. when the arrangement of the status fields corresponds to the spatial arrangement of the related (local and remote) patient monitors.

Figure 4C:
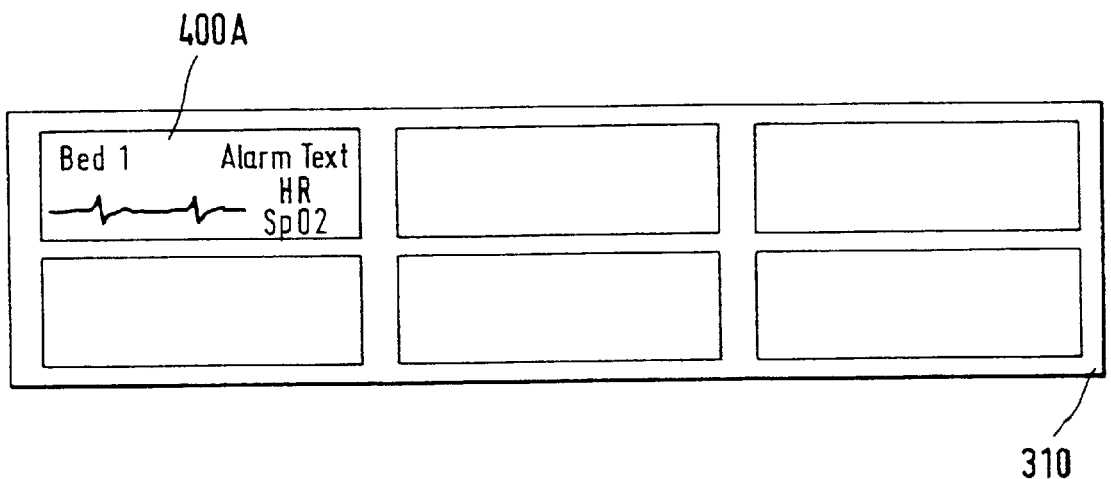

FIG. 4C shows another example of the overview area 310. If, for example in the embodiment of FIGS. 4A and 4B, the permanently visible overview area 310 of the remote patient monitors is enlarged, the status of an individual patient monitor can be extended to display more or more detailed information. In the example of FIG. 4C, the upper left status field 400A shows a bed label, alarms, a subset of parameters and one wave for the respective related patient monitor.

Figure 4D:
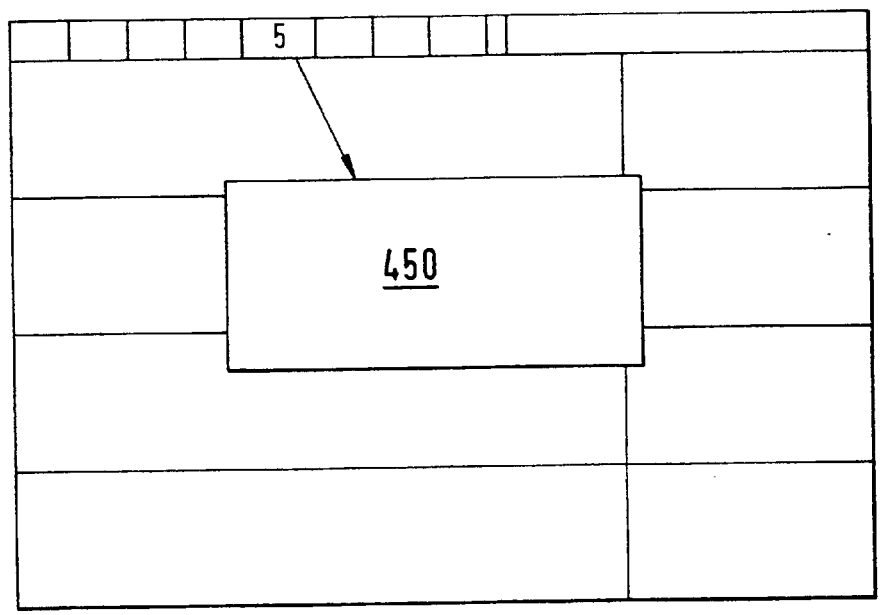

In a preferred embodiment as depicted in FIG. 4D, the overview area 310 can also be used as entry point for operations to get more or more detailed information about one or more of the related patient monitors, or to invoke a remote operation such as to silence an alarm or to change alarm limits. In the example of FIG. 4D, a pop-up window 450 will be opened by selecting (e.g. clicking on) the status fields 400E represented by a numeric sign "5". The pop-up window 450 represents data of the (remote) patient monitor assigned by the numeric sign "5" and can be further processed as known in the art.

What is claimed is:

1. A local patient monitor for monitoring the physiological condition of a local patient, adapted to provide a data-communication with one or more remote patient monitors in a network, and; a display for displaying information, wherein the display comprises an overview area for displaying status information from the one or more remote patient monitors, the overview area providing the status information continuously and independently of an alarming situation by displaying said status information, the providing of the status information occurring without the need for a prior user interaction to invoke said providing of said status information.

2. The local patient monitor of claim 1, wherein the overview area is a side area of the display.

3. The local patient monitor of claim 1, wherein the overview area is spatially separated from other display areas of the display for displaying other information, whereby the local patient monitor further comprises means for ensuring that the other display areas will not overlap the overview area on user request.

4. The local patient monitor of claim 1, wherein the overview area remains permanently allocated within the display.

5. The local patient monitor of claim 1, wherein the overview area comprises items selected from the group of symbols, codes, pictograms, graphical data curves, or alphanumerical text fields for displaying the status information.

6. The local patient monitor of claim 1, wherein the size of the overview area comprises at least one entry point for operations to get more information from one or more of the remote patient monitors.

7. The local patient monitor of claim 1, wherein said information is representative of the physiological condition of the local patient.

8. The local patient monitor of claim 1, wherein said network further comprises a central data-display component.

9. The local patient monitor of claim 1, wherein the overview area is separated from other data to be displayed.

10. The local patient monitor of claim 1, wherein the overview area is spatially separated from other display areas of the display for displaying other information, whereby the local patient monitor further comprises means for ensuring that the other display areas only temporarily overlap the overview area on user request.

11. The local patient monitor of claim 1, wherein the overview area remains allocated within the display at least as long as defined by a respective application.

12. The local patient monitor of claim 1, wherein the overview area remains allocated within the display at least as long as defined by a user.

13. The local patient monitor of claim 1, wherein said providing of said status information occurs independently of a size of the overview area.

14. The local patient monitor of claim 1, wherein the overview area provides said status information by displaying said status information, the providing of the status information occurring independently of a size of the overview area.

15. A patient monitoring system comprising: a plurality of patient monitors, each adapted for monitoring the physiological condition of a local patient connected with the respective patient monitor, whereby the patient monitors are adapted to provide a data-communication with each other, and each patient monitor comprises a display adapted for displaying information representative of the physiological condition of the local patient, wherein the display of at least one of the patient monitors comprises an overview area for displaying status information from one or more of the other patient monitors, the overview area providing the status information continuously and independently of an alarming situation by displaying said status information, the providing of the status information occurring without the need for a prior user interaction to invoke said providing of said status information.

16. A method for monitoring the physiological condition of a local patient with a local patient monitor adapted to provide a data-communication with one or more remote patient monitors in a network, the method comprising the steps of:

displaying, on a display, information representative of the physiological condition of the local patient, and displaying, in an overview area of a display, status information from the one or more remote patient monitors, the overview area providing the status information continuously and independently of an alarming situation by displaying said status information, the providing of the status information occurring without the need for a prior user interaction to invoke said providing of said status information.

17. A software program, adapted to be stored on or otherwise provided by any kind of data carrier, for executing the steps of the method of claim 16 when run in or by any suitable data processing unit.

18. A method according to claim 16 wherein said network further comprises a central data-display component.

* * * * *